United States Patent
Lozier et al.

(10) Patent No.: US 8,435,305 B2
(45) Date of Patent: May 7, 2013

(54) OSTEOCHONDRAL GRAFT DELIVERY DEVICE AND USES THEREOF

(75) Inventors: Antony J. Lozier, Warsaw, IN (US); Daniel P. Murphy, Claypool, IN (US)

(73) Assignee: Zimmer, Inc., Warsaw, IN (US)

( * ) Notice: Subject to any disclaimer, the term of this patent is extended or adjusted under 35 U.S.C. 154(b) by 176 days.

(21) Appl. No.: 12/873,049

(22) Filed: Aug. 31, 2010

(65) Prior Publication Data

US 2012/0053642 A1   Mar. 1, 2012

(51) Int. Cl.
*A61F 2/28* (2006.01)
(52) U.S. Cl.
USPC ................. 623/23.48; 606/86 R; 606/99
(58) Field of Classification Search ........ 606/86 A, 606/86 B, 86 R, 92–95, 99, 104, 107, 914, 606/915, 916, 14–16, 57, 59–64, 218; 623/13.11, 623/13.14, 13.15, 14.12, 23.48; 294/100; 401/93
See application file for complete search history.

(56) References Cited

U.S. PATENT DOCUMENTS

| | | | |
|---|---|---|---|
| 1,567,910 A * | 12/1925 | Brynda et al. ............. 401/33 |
| 1,703,154 A | 2/1929 | Lanzkron | |
| 1,984,839 A | 12/1934 | Murray | |
| 3,564,947 A | 2/1971 | Maier | |
| 3,564,948 A | 2/1971 | Pomernacki | |
| 3,848,601 A | 11/1974 | Ma | |
| 3,971,273 A | 7/1976 | Peters et al. | |
| 4,010,737 A | 3/1977 | Vilaghy et al. | |
| 4,250,892 A | 2/1981 | Dolhay et al. | |
| 4,589,206 A | 5/1986 | Marcoux | |
| 4,706,659 A | 11/1987 | Matthews et al. | |
| 5,067,964 A | 11/1991 | Richmond et al. | |
| 5,115,704 A | 5/1992 | Hyman | |
| 5,139,520 A | 8/1992 | Rosenberg | |
| 5,152,791 A | 10/1992 | Hakamatsuka et al. | |
| 5,184,926 A | 2/1993 | Hemmings | |

(Continued)

FOREIGN PATENT DOCUMENTS

| AU | 4922296 A | 9/1996 |
|---|---|---|
| DE | 2411618 A1 | 4/1975 |

(Continued)

OTHER PUBLICATIONS

"U.S. Appl. No. 12/045,416, Response filed Jul. 17, 2012 to Final Office Action mailed Feb. 17, 2012", 19 pgs.

(Continued)

*Primary Examiner* — Todd Manahan
*Assistant Examiner* — Eric S Gibson
(74) *Attorney, Agent, or Firm* — Schwegman, Lundberg & Woessner P.A.

(57) ABSTRACT

A delivery device for an osteochondral graft comprising a tube, a plunger and a graft retention assembly is disclosed. The tube has a bore having an inside diameter and extends from a proximal end to a distal end. The inside diameter of the bore is sufficient to accept an osteochondral graft of a desired diameter. The tube has a set of apertures located adjacent the distal end of the tube. The plunger is slidably disposed within the bore of the tube. The graft retention assembly comprises a collar and a set of tabs. The graft retention assembly is attached to the tube such that the tabs are disposed within the apertures of the tube. The tabs are biased towards each other but are capable of being displaced away from each other to receive or release the osteochondral graft.

20 Claims, 4 Drawing Sheets

U.S. PATENT DOCUMENTS

| | | | |
|---|---|---|---|
| 5,197,833 A | 3/1993 | Mayer et al. | |
| 5,328,722 A | 7/1994 | Ghanayem et al. | |
| 5,341,816 A | 8/1994 | Allen | |
| 5,362,166 A * | 11/1994 | Yamamoto et al. | 401/93 |
| 5,368,051 A | 11/1994 | Dunn et al. | |
| 5,370,692 A | 12/1994 | Fink et al. | |
| 5,423,823 A | 6/1995 | Schmieding | |
| 5,425,490 A | 6/1995 | Goble et al. | |
| 5,443,468 A | 8/1995 | Johnson | |
| 5,575,798 A | 11/1996 | Koutrouvelis | |
| 5,591,234 A | 1/1997 | Kirsch | |
| 5,632,745 A | 5/1997 | Schwartz | |
| 5,632,747 A | 5/1997 | Scarborough et al. | |
| 5,718,707 A | 2/1998 | Mikhail | |
| 5,788,713 A | 8/1998 | Dubach | |
| 5,810,887 A | 9/1998 | Accorti, Jr. et al. | |
| 5,860,946 A * | 1/1999 | Hofstatter | 604/15 |
| 5,876,452 A | 3/1999 | Athanasiou et al. | |
| 5,899,860 A | 5/1999 | Pfeiffer et al. | |
| 5,904,717 A | 5/1999 | Brekke et al. | |
| 5,919,196 A | 7/1999 | Bobic et al. | |
| 5,921,987 A | 7/1999 | Stone | |
| 6,110,178 A | 8/2000 | Zech et al. | |
| 6,231,608 B1 | 5/2001 | Stone | |
| 6,270,503 B1 | 8/2001 | Schmieding | |
| 6,306,142 B1 | 10/2001 | Johanson et al. | |
| 6,358,253 B1 | 3/2002 | Torrie et al. | |
| 6,375,658 B1 | 4/2002 | Hangody et al. | |
| 6,395,011 B1 | 5/2002 | Johanson et al. | |
| 6,488,033 B1 | 12/2002 | Cerundolo | |
| 6,530,928 B1 | 3/2003 | Frei et al. | |
| 6,582,438 B2 | 6/2003 | DeMayo | |
| 6,591,581 B2 | 7/2003 | Schmieding | |
| 6,592,588 B1 | 7/2003 | Bobic et al. | |
| 6,767,354 B2 | 7/2004 | Johanson et al. | |
| 6,793,429 B2 * | 9/2004 | Arrison | 401/93 |
| 6,852,114 B2 | 2/2005 | Cerundolo | |
| 6,988,015 B1 | 1/2006 | Schopf et al. | |
| 6,998,418 B1 | 2/2006 | Sung et al. | |
| 7,048,477 B2 | 5/2006 | Abrams | |
| 7,160,305 B2 | 1/2007 | Schmieding | |
| 7,264,634 B2 | 9/2007 | Schmieding | |
| 7,371,260 B2 | 5/2008 | Malinin | |
| 7,416,371 B2 | 8/2008 | Scott et al. | |
| 7,548,865 B2 | 6/2009 | Schmieding | |
| 7,550,007 B2 | 6/2009 | Malinin | |
| 7,563,266 B2 | 7/2009 | Camino et al. | |
| 7,572,291 B2 | 8/2009 | Gil et al. | |
| 7,591,820 B2 | 9/2009 | Schmieding et al. | |
| 7,608,098 B1 | 10/2009 | Stone et al. | |
| 7,666,230 B2 | 2/2010 | Orban et al. | |
| 7,758,583 B2 | 7/2010 | Gil et al. | |
| 7,776,043 B2 | 8/2010 | Hycz et al. | |
| 7,833,269 B2 | 11/2010 | Nycz et al. | |
| 7,862,567 B2 | 1/2011 | Schmieding | |
| 7,875,032 B2 | 1/2011 | Lyons | |
| 7,879,040 B2 | 2/2011 | Bharadwaj | |
| 7,887,546 B2 | 2/2011 | Gil et al. | |
| 7,905,904 B2 | 3/2011 | Stone et al. | |
| 7,909,851 B2 | 3/2011 | Stone et al. | |
| 7,909,873 B2 | 3/2011 | Tan-Malecki et al. | |
| 7,914,539 B2 | 3/2011 | Stone et al. | |
| 7,955,335 B2 | 6/2011 | Gil et al. | |
| 7,955,336 B2 | 6/2011 | Gil et al. | |
| 7,985,230 B2 | 7/2011 | Gil et al. | |
| 7,997,174 B2 | 8/2011 | Gil et al. | |
| 8,034,090 B2 | 10/2011 | Stone et al. | |
| 8,048,079 B2 | 11/2011 | Iannarone | |
| RE43,714 E | 10/2012 | Nadler et al. | |
| 2003/0171810 A1 | 9/2003 | Steiner | |
| 2004/0039400 A1 | 2/2004 | Schmieding et al. | |
| 2004/0193154 A1 | 9/2004 | Leatherbury et al. | |
| 2004/0230194 A1 * | 11/2004 | Urbanski et al. | 606/68 |
| 2005/0013872 A1 | 1/2005 | Freyman | |
| 2005/0021044 A1 | 1/2005 | Stone et al. | |
| 2005/0038520 A1 | 2/2005 | Bienette et al. | |
| 2005/0080435 A1 | 4/2005 | Smith et al. | |
| 2005/0137600 A1 | 6/2005 | Jacobs et al. | |
| 2006/0131906 A1 * | 6/2006 | Maurer et al. | 294/100 |
| 2006/0247790 A1 | 11/2006 | McKay | |
| 2007/0043376 A1 * | 2/2007 | Leatherbury et al. | 606/99 |
| 2007/0135917 A1 | 6/2007 | Malinin | |
| 2007/0135918 A1 | 6/2007 | Malinin | |
| 2007/0149982 A1 | 6/2007 | Lyons | |
| 2007/0270711 A1 | 11/2007 | Gil et al. | |
| 2008/0051812 A1 | 2/2008 | Schmitz et al. | |
| 2008/0167653 A1 | 7/2008 | Watlington et al. | |
| 2008/0195115 A1 | 8/2008 | Oren et al. | |
| 2008/0200915 A1 | 8/2008 | Globerman et al. | |
| 2008/0243028 A1 | 10/2008 | Howard et al. | |
| 2008/0243029 A1 | 10/2008 | Howard et al. | |
| 2008/0255427 A1 | 10/2008 | Satake et al. | |
| 2008/0262616 A1 | 10/2008 | McKay | |
| 2008/0269566 A1 | 10/2008 | Measamer et al. | |
| 2008/0306608 A1 | 12/2008 | Nycz et al. | |
| 2009/0024224 A1 | 1/2009 | Chen et al. | |
| 2009/0054906 A1 * | 2/2009 | Walthall et al. | 606/108 |
| 2009/0171359 A1 | 7/2009 | Sterrett | |
| 2009/0209962 A1 | 8/2009 | Jamali | |
| 2009/0275950 A1 | 11/2009 | Sterrett et al. | |
| 2009/0281550 A1 * | 11/2009 | Keller | 606/99 |
| 2009/0299371 A1 | 12/2009 | Steiner et al. | |
| 2009/0299372 A1 | 12/2009 | Steiner et al. | |
| 2009/0319051 A9 | 12/2009 | Nycz et al. | |
| 2010/0168750 A1 | 7/2010 | Sherman | |
| 2010/0249786 A1 | 9/2010 | Schmieding et al. | |
| 2010/0292704 A1 | 11/2010 | Stoffel et al. | |
| 2011/0009872 A1 * | 1/2011 | Mistry et al. | 606/99 |
| 2011/0046628 A1 | 2/2011 | Jamali | |
| 2011/0054408 A1 | 3/2011 | Wei et al. | |
| 2011/0137315 A1 | 6/2011 | Gil et al. | |
| 2011/0144648 A1 | 6/2011 | Gil et al. | |
| 2011/0208193 A1 | 8/2011 | Gil et al. | |
| 2012/0053588 A1 | 3/2012 | Lozier et al. | |

FOREIGN PATENT DOCUMENTS

| | | |
|---|---|---|
| DE | 2933174 A1 | 4/1980 |
| DE | 4317448 A1 | 11/1994 |
| DE | 19503504 A1 | 3/1996 |
| EP | 0307241 A2 | 3/1989 |
| EP | 0493698 A1 | 7/1992 |
| EP | 0508710 A1 | 10/1992 |
| EP | 0768332 A1 | 4/1997 |
| EP | 0815809 A2 | 1/1998 |
| EP | 0824893 A2 | 2/1998 |
| FR | 2700462 A1 | 7/1994 |
| GB | 2175506 A | 12/1986 |
| JP | 3178652 A | 2/1991 |
| JP | 4303450 A | 10/1992 |
| JP | 9122226 A | 5/1997 |
| JP | 10251492 A | 9/1998 |
| JP | 10513386 A | 12/1998 |
| WO | WO-9315694 A1 | 8/1993 |
| WO | WO-9426211 A1 | 11/1994 |
| WO | WO-9624302 A1 | 8/1996 |
| WO | WO-9624310 A1 | 8/1996 |
| WO | WO-9627333 A1 | 9/1996 |
| WO | WO-9725942 A1 | 7/1997 |
| WO | WO-9746665 A1 | 12/1997 |
| WO | WO-9834569 A1 | 8/1998 |
| WO | WO-9834596 A2 | 8/1998 |
| WO | WO-9840027 A1 | 9/1998 |
| WO | WO-9856317 A1 | 12/1998 |
| WO | WO-0143667 A1 | 6/2001 |
| WO | WO-0224244 A2 | 3/2002 |
| WO | WO-2005023321 A2 | 3/2005 |
| WO | WO-2005094694 A2 | 10/2005 |
| WO | WO-2006026325 A2 | 3/2006 |
| WO | WO-2008/147692 A1 | 12/2008 |
| WO | WO-2010092100 A1 | 8/2010 |
| WO | WO-2011008968 A1 | 1/2011 |

OTHER PUBLICATIONS

"U.S. Appl. No. 12/873,030, Restriction Requirement mailed Jul. 10, 2012", 6 pgs.

"U.S. Appl. No. 11/705,575, Notice of Allowance mailed May 15, 2012", 5 pgs.

"U.S. Appl. No. 11/705,575, Response filed Dec. 15, 2011 to Non Final Office Action mailed Sep. 15, 2011", 14 pgs.

"U.S. Appl. No. 12/045,416, Final Office Action mailed Feb. 17, 2012", 13 pgs.

"U.S. Appl. No. 12/045,416, Response filed Dec. 5, 2011 to Non Final Office Action mailed Aug. 4, 2011", 18 pgs.

"U.S. Appl. No. 12/196,831, Advisory Action mailed Jul. 5, 2012", 3 pgs.

"U.S. Appl. No. 12/196,831, Examiner Interview Summary mailed Feb. 6, 2012", 18 pgs.

"U.S. Appl. No. 12/196,831, Final Office Action mailed Apr. 12, 2012", 17 pgs.

"U.S. Appl. No. 12/196,831, Response filed Feb. 1, 2012 to Non Final Office Action mailed Oct. 6, 2011", 15 pgs.

"U.S. Appl. No. 12/196,831, Response filed Jun. 12, 2012 to Final Office Action mailed Apr. 12, 2012", 14 pgs.

"U.S. Appl. No. 12/196,831, Response filed Sep. 12, 2012 to Advisory Action mailed Jul. 5, 2012", 16 pgs.

"U.S. Appl. No. 12/873,030, Response filed Jul. 27, 2012 to Restriction Requirement mailed Jul. 10, 2012", 7 pgs.

Bobic, V, "Arthroscopic osteochondral autograft transplantation in anterior cruciate ligament reconstruction: a preliminary clinical study", Knee Surg, Sport Traumatol, Arthroscopy 3, (1996), 262-264.

Convery, F.R., et al., "The Repair of Large Osteochondral Defects", An Experimental Study in Horses, Clin. Orthrop. 82., (1972), 253-262.

Ehalt, W, "Bisherige Erfahrungen mit dem plastischen Ersatz von Gelenkknorpel aus der Knochenbank", Verh. Dtsch. Orthop. Ges. 43, (1955), 107-109.

Ehalt, W., et al., "Gelenkknorpel-Plastik", Langenbecks Arch. Kiln. Chir. 299, (1962), 768-774.

Ehalt, Walther M, "Grafting of joint-cartilage Bone-Blocks from the bank", VI. Congr. Soc. Internat. Chir. Orthop. Traumatol. S., (1954), 419-421.

Garrett, John C, "Treatment of Osteochondral Defects of the Distal Femur with Fresh Osteochondral Allografts: A Preliminary Report", Arthroscopy: The Journal of Arthroscopic and Related Surgery 2(4), (1986), 222-226.

Guhl, James F, "Chapter 21: The Impact of Arthroscopy on Osteochondritis Dissecans", Operative Arthroscopy, (1991), 297-317.

Hangody, L, et al., "Autogenous osteochondral grafting in the knees of German Shepherd dogs: Radiographic and histological analysis", Hungarian Review of Sports Medicine 35, (1994), 117-123.

Hangody, L, et al., "Treatment of localized chondral and osteochondral defects in the knee by a new autogenous osteochondral grafting tenique", Hungarian Review of Sports Medicine 35, (1994), 241-246.

Hangody, Laszlo, "Arthroscopic autogeous osteochondral mosaicplasty for the treatment of femoral condylar articular defects: A preliminary report", Knee Surg, Sports Traumatol, Arthrosc 5, (1997), 262-267.

Hangody, Laszlo, et al., "Artoszkopos autolog osteochondralis mozaikplastica (Arthroscopic autogenous osteochondral mosaicplasty)", Hungarian Journal of Traumatology and Orthopaedics 39, (1996), 49-54.

Hangody, Laszlo, "Autologous osteochondral mosaic-like graft technique for replacing weight bearing cartilage defects", 7th Congress of ESSTKSA, Abstract Only, (1996), 3 pgs.

Hangody, Laszlo, et al., "Autologous Osteochondral Mosaic-Plasty", Review of Osteology 3, (1996), 70-73.

Hangody, Laszlo, "Chapter 13: Autogenous Osteochondral Mosaicplasty for the Treatment of Focal Chondral and Osteochondral Defects of the Femoral Condyles", Knieinstabilitat und Knorpelschaden, (1998), 97-106.

Hangody, Laszlo, "Mosaic-plasty in Clinical Practice", Review of Osteology 4, (1996), 32-36.

Hangody, Laszlo, et al., "Mosaicplasty for the Treatment of Articular Cartilage Defects: Application in Clinical Practice", Orthopedics 21(2), (1998), 751-756.

Hangody, Laszlo, et al., "Mosaicplasty for the treatment of osteochondritis dissecans of the knee", [Online]. Retrieved from the Internet: <URL: http://www.egydoc.com/Sites/Arthroclub/AC_Files/Articles/article39.pdf>, (Accessed Nov. 8, 2005), 9 pgs.

Hangody, Laszlo, et al., "New Method in Treatment of Sever Local Cartilage Damage in the Knee Joint (Eine neue Methode in der Behandlung von schweren, lokalen Knorpelschaden im Kniegelenk", Osteosynthese International 5, (1997), 316-321.

Hangody, Laszlo, et al., "Osteochondral Plugs: Autogenous Osteochondral Mosaicplasty for the Treatment of Focal Chondral and Osteochondral Articular Defects", Operative Techniques in Orthopaedics 7(4), (1997), 312-322.

Hangody, Laszlo, et al., "Sülyos, körülírt térdízületi porckárosodás sebészi kezelésének új lehetosége (New alternative in the treatment of sever, localized cartilage damages in the knee joint)", Hungarian Journal of Traumatology and Orthopaedics 37, (1994), 237-242.

Hangody, Laszlo, et al., "Treatment of Osteochondritis Dissecans of the Talus: Use of Mosaicplasty Technique—A Preliminary Report", Foot and Ankle International 18(10), (1997), 628-634.

Lindholm, Sam, et al., "Reconstruction of the Articular Surface by Transfixation of an Osteochondral Fragment of the Femoral Condyle Using a Bone Transplant", Scandinavian Journal of Rheumatology Supplement 44, (1982), 5-13.

Muller, W, "Osteochondrosis Dissecans", Progress in Orthopaedic Surgery vol. 3, (1978), 135-142.

Woods, T, "Effectiveness of three extraction techniques in the development of a decellularized bone-anterior cruciate ligament-bone graft", Biomaterials, Elsevier Science Publishers BV., Barking, GB, vol. 26, No. 35, (Dec. 1, 2005), 7339-7349.

Yamashita, et al., "The Transplantation of an Autogeneic Osteochondral Fragment for Osteochondritis Dissecans of the Knee", Clinical Orthopaedics and Related Research, No. 201, (1985), 43-50.

"U.S. Appl. No. 10/149,853, Non Final Office Action mailed Apr. 13, 2004", 8 pgs.

"U.S. Appl. No. 10/149,853, Notice of Allowance mailed Oct. 5, 2004", 7 pgs.

"U.S. Appl. No. 10/149,853, Preliminary Amendment mailed Oct. 17, 2002", 6 pgs.

"U.S. Appl. No. 10/149,853, Response filed Jul. 6, 2004 to Non Final Office Action mailed Apr. 13, 2004", 9 pgs.

"U.S. Appl. No. 11/705,575, Non Final Office Action mailed Mar. 16, 2005", 9 pgs.

"U.S. Appl. No. 11/705,575, Non Final Office Action mailed Sep. 15, 2011", 8 pgs.

"U.S. Appl. No. 11/705,575, Notice of Non-Compliant Amendment mailed Jan. 7, 2011", 3 pgs.

"U.S. Appl. No. 11/705,575, Notice of Non-Compliant Amendment mailed Oct. 29, 2010", 3 pgs.

"U.S. Appl. No. 11/705,575, Preliminary Amendment filed Feb. 12, 2007", 14 pgs.

"U.S. Appl. No. 11/705,575, Response flied Feb. 7, 2011 to Notice of Non-Compliant Amendment mailed Jan. 7, 2011", 22 pgs.

"U.S. Appl. No. 11/705,575, Response filed Sep. 15, 2010 to Non Final Office Action mailed Mar. 16, 2010", 13 pgs.

"U.S. Appl. No. 11/705,575, Response filed Nov. 29, 2010 to Notice of Non-Compliant Amendment mailed Oct. 29, 2010", 14 pgs.

"U.S. Appl. No. 11/705,575, Revised Preliminary Amendment filed Sep. 15, 2010 in Response to Office Action mailed Mar. 16, 2010", 11 pgs.

"U.S. Appl. No. 11/753,102, Advisory Action filed Dec. 10, 2010", 3 pgs.

"U.S. Appl. No. 11/753,102, Final Office Action mailed Aug. 3, 2010", 15 pgs.

"U.S. Appl. No. 11/753,102, Non Final Office Action mailed Jan. 4, 2010", 23 pgs.

"U.S. Appl. No. 11/753,102, Response filed May 4, 2010 to Non Final Office Action mailed Jan. 4, 2010", 13 pgs.

"U.S. Appl. No. 11/753,102, Response filed Nov. 23, 2009 to Restriction Requirement mailed Oct. 30, 2009", 12 pgs.

"U.S. Appl. No. 11/753,102, Response filed Dec. 3, 2010 to Final Office Action mailed Aug. 3, 2010", 15 pgs.

"U.S. Appl. No. 11/753,102, Restriction Requirement mailed Oct. 30, 2009", 9 pgs.

"U.S. Appl. No. 11/759,679, Final Office Action mailed Oct. 7, 2010", 17 pgs.

"U.S. Appl. No. 11/759,679, Non Final Office Action mailed Feb. 26, 2010", 14 pgs.

"U.S. Appl. No. 11/759,679, Response filed Jun. 28, 2009 to Non Final Office Action mailed Feb. 26, 2010", 13 pgs.

"U.S. Appl. No. 11/759,679, Response filed Oct. 30, 2009 to Restriction Requirement mailed Sep. 4, 2009", 3 pgs.

"U.S. Appl. No. 11/759,679, Restriction Requirement mailed Sep. 4, 2009", 6 pgs.

"U.S. Appl. No. 12/045,416, Non Final Office Action mailed Aug. 4, 2011", 12 pgs.

"U.S. Appl. No. 12/045,416, Response filed Jun. 2, 2011 to Restriction Requirement mailed May 11, 2011", 13 pgs.

"U.S. Appl. No. 12/045,416, Restriction Requirement mailed May 11, 2011", 8 pgs.

"U.S. Appl. No. 12/196,831, Advisory Action mailed Jan. 21, 2011", 3 pgs.

"U.S. Appl. No. 12/196,831, Final Office Action mailed Nov. 12, 2010", 10 pgs.

"U.S. Appl. No. 12/196,831, Non Final Office Action mailed Jul. 9, 2010", 7 pgs.

"U.S. Appl. No. 12/196,831, Non Final Office Action mailed Oct. 6, 2011", 8 pgs.

"U.S. Appl. No. 12/196,831, Response filed Jan. 10, 2011 to Final Office Action mailed Nov. 12, 2010", 10 pgs.

"U.S. Appl. No. 12/196,831, Response filed Jun. 21, 2010 to Restriction Requirement mailed Jun. 8, 2010", 8 pgs.

"U.S. Appl. No. 12/196,831, Response filed Oct. 7, 2010 to Non Final Office Action mailed Jul. 9, 2010", 11 pgs.

"U.S. Appl. No. 12/196,831, Restriction Requirement mailed Jun. 8, 2010", 7 pgs.

"International Application Serial No. PCT/US2008/063582, International Search Report mailed Oct. 9, 2008", 3 pgs.

"International Application Serial No. PCT/US2008/063582, Written Opinion mailed Oct. 9, 2008", 7 pgs.

International Application Serial No. PCT/US2008/064653, International Search Report mailed Sep. 7, 2009 3 pgs.

"International Application Serial No. PCT/US2008/064653, Written Opinion mailed Sep. 7, 2009", 8 pgs.

"International Application Serial No. PCT/US2009/038661, International Search Report mailed Jun. 12, 2009", 4 pgs.

"International Application Serial No. PCT/US2009/036661, Written Opinion mailed Jun. 12, 2009", 8 pgs.

Garrett, J. C., "Chapter 34—Osteochondral Allografts", 355-358.

"U.S. Appl. No. 12/873,030, Response filed Feb. 28, 2013 to Non Final Office Action mailed Oct. 30, 2012", 14 pgs.

"Australian Application Serial No. 200116857, Office Action mailed Feb. 13, 2004", 2 pgs.

"Canadian Application Serial No. 00979315.9, Office Action mailed Jan. 24, 2007", 3 pgs.

"Canadian Application Serial No. 00979315.9, Response filed Jul. 23, 2007 to Office Action mailed Jan. 24, 2007", 14 pgs.

"European Application Serial No. 04020622.9, European Search Report mailed Nov. 29, 2004", 6 pgs.

"European Application Serial No. 04020622.9, Office Action mailed Oct. 20, 2005", 3 pgs.

"European Application Serial No. 04020622.9, Response filed Apr. 13, 2006 to Office Action mailed Oct. 20, 2005", 12 pgs.

"International Application Serial No. PCT/CH00/00659, International Preliminary Examination Report mailed Mar. 20, 2002", 15 pgs.

"International Application Serial No. PCT/CH00/00659, International Search Report mailed Jan. 2, 2001", 8 pgs.

"International Application Serial No. PCT/US2008/063582, International Preliminary Report on Patentability mailed Nov. 24, 2009", 8 pgs.

"International Application Serial No. PCT/US2009/036661, International Preliminary Report on Patentability mailed Sep. 14, 2010", 9 pgs.

"Japanese Application Serial No. 2000-544609, Office Action mailed Jan. 5, 2010", 9 pgs.

"Japanese Application Serial No. 2000-544609, Office Action mailed Mar. 24, 2009", 8 pgs.

"Japanese Application Serial No. 2000-544609, Office Action mailed Aug. 5, 2008", 5 pgs.

"Japanese Application Serial No. 2000-544609, Office Action mailed Nov. 2, 2010", 7 pgs.

"Japanese Application Serial No. 2000-544609, Response filed Apr. 27, 2010 to Office Action mailed Jan. 24, 2010", 8 pgs.

"Japanese Application Serial No. 2000-544609, Response filed Jun. 11, 2009 to Office Action mailed Mar. 24, 2009", 14 pgs.

"Japanese Application Serial No. 2000-544609, Response filed Oct. 28, 2008 to Office Action mailed Aug. 5, 2008", 14 pgs.

"U.S. Appl. No. 12/873,030, Non Final Office Action mailed Oct. 30, 2012", 17 pgs.

Albee, Fred H, "Bone Surgery With Machine Tools", Scientific American vol. 154.4, (Apr. 1936), 5 pgs.

* cited by examiner

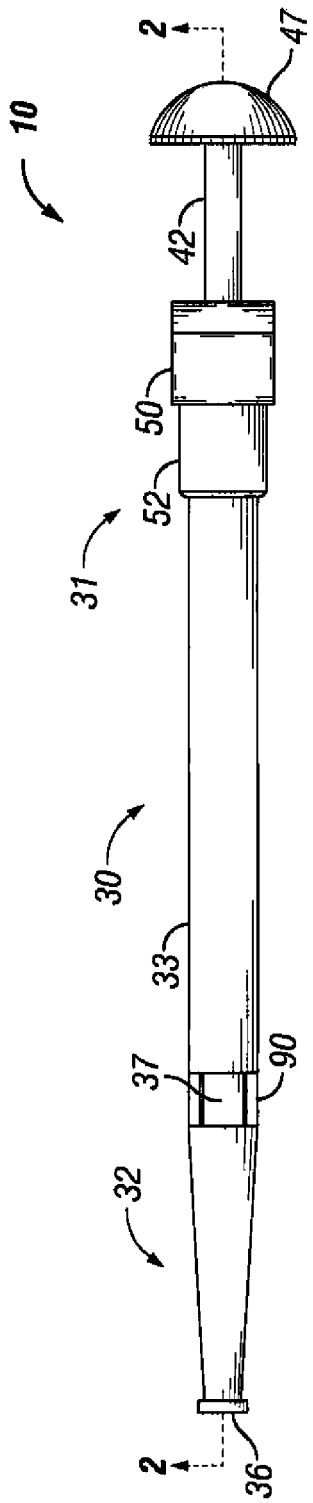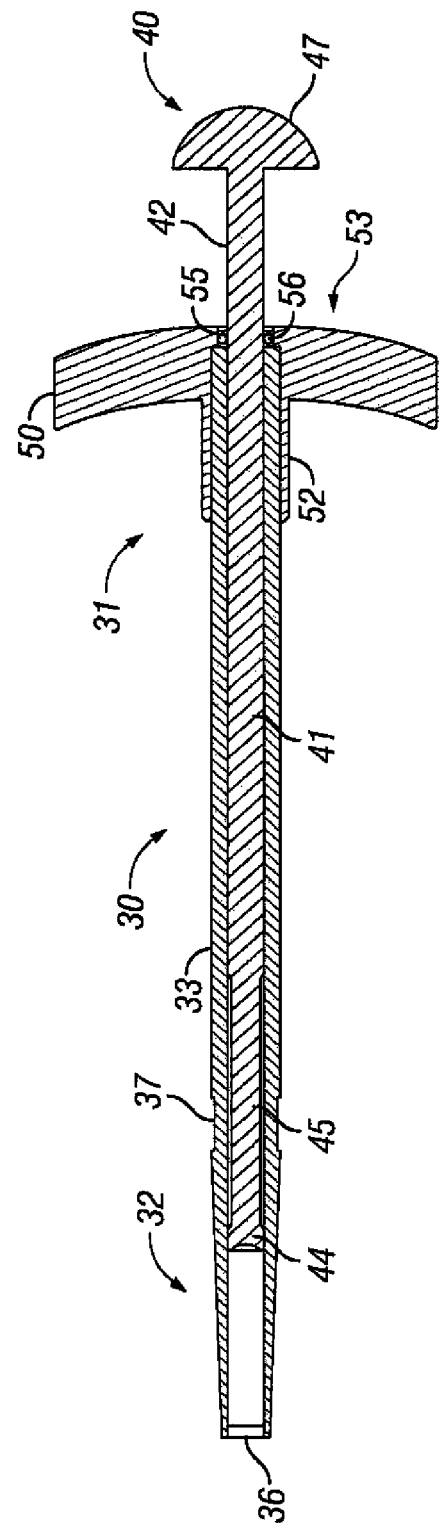

OSTEOCHONDRAL GRAFT DELIVERY DEVICE AND USES THEREOF

BACKGROUND

The present invention relates to instrumentation used in implantation of an osteochondral graft, more particularly, to a delivery device used in inserting the osteochondral graft in a previously prepared hole. The invention also relates to the use of the delivery device to implant an osteochondral graft.

The delivery device of the present invention can also be used or adapted for use with bone-only or cartilage-only grafts or grafts of other construction, including artificial grafts, such as non-tissue grafts made from metals and synthetic materials. The invention has particular utility in repairing localized damage to bone and cartilage, such as lesions and other defects in an articular surface of the knee or other weight-articulating joints.

The knee and other articulating joints are susceptible to lesions and other defects. These may be the result of injuries caused by friction between opposing bone surfaces. While treatment options for these injuries lie along a continuum of care culminating in joint replacement, one treatment option is to replace the osteochondral tissue at the site of the injury with a graft of healthy tissue. Typically, autografts or allografts are employed; however, xenografts and artificial grafts, as previously described, may be employed. The surgery to implant these grafts often can be conducted arthroscopically. For this and other reasons, graft implantation may be more desirable than joint replacement.

The procedure for implanting osteochondral grafts involves creating a recipient site by removing the localized defect. Typically, this is done by forming a hole of a desired diameter (or holes, potentially, depending on the size of the defect) at the site of the damage. The hole may be bored, punched, or curetted, etc. The excised hole is then filled with a replacement osteochondral graft having a diameter corresponding to the diameter of the hole. The typical graft is cylindrical in shape and consists of a layer of cartilage over a layer of bone. Depending on the size of the damage, multiple holes of the same or different diameters may be bored and filled. Generally, in such instances, one hole will be bored and then filled before an adjacent or even overlapping hole is bored and filled.

Varied instrumentation is required throughout the surgery, both for forming the hole and implanting the replacement graft. Certain instrumentation may be tailored to the specific implant diameter.

Due to the delicate nature of the implantation procedure, in that its ultimate purpose is to repair or replace the articular surface and restore normal function to the joint, the method by which the transplanted osteochondral graft is handled and introduced into the recipient site is of particular importance. A desirable delivery device would provide a means for securely holding onto the osteochondral graft so that it is not displaced from the delivery device prematurely while simultaneously avoiding damage to the osteochondral graft.

SUMMARY

The present invention relates to instrumentation used in implantation of an osteochondral graft, more particularly, to a delivery device used in inserting the osteochondral graft in a previously prepared hole. The invention also relates to the use of the delivery device to implant an osteochondral graft.

The delivery device of the present invention can also be used or adapted for use with bone-only or cartilage-only grafts or grafts of other construction, including artificial grafts, such as non-tissue grafts made from metals and synthetic materials. The invention has particular utility in repairing localized damage to bone and cartilage, such as lesions and other defects in an articular surface of the knee or other weight-articulating joints.

According to one aspect of the invention, there is provided a delivery device for an osteochondral graft. The delivery device has a tube, a plunger and a graft retention assembly. The tube comprises a bore, having an inside diameter, that extends from a proximal end to a distal end. The inside diameter of the bore is sufficient to accept an osteochondral graft of a desired diameter. A set of apertures are located adjacent the distal end of the tube. The plunger, slidably disposed within the bore of the tube, comprises a shaft having a proximal end, distal end, and distal tip. The graft retention assembly comprises a collar and a set of tabs, which are disposed within the apertures of the tube. The tabs are biased towards each other but are capable of being displaced away from each other to receive or release the osteochondral graft. The graft retention assembly may be attached to the tube at an annular recess located along an outside diameter of the tube proximal to the apertures by means of the collar.

The delivery device may further comprise a handle positioned at the proximal end of the tube, with the handle comprising a bore extending from a proximal end to a distal end, and the bore having an inside diameter at its distal end sufficient to accept an outside diameter of the proximal end of the tube. The handle may further comprise an annular recess located at the proximal end of its bore that can accommodate a pliable material providing frictional engagement with the shaft of the plunger.

In accordance with another aspect of the present invention, there is also provided a delivery device for an osteochondral graft comprising a tube, a plunger, a graft retention assembly, and a handle. The tube comprises a bore, having an inside diameter, that extends from a proximal end to a distal end. The inside diameter of bore is sufficient to accept an osteochondral graft of a desired diameter. A set of apertures are located adjacent the distal end of the tube, and an annular recess is located along an outside diameter of the tube proximal to the apertures.

The plunger, slidably disposed within the bore of the tube, comprises a shaft having a proximal end, distal end, and distal tip. The plunger has a handle positioned at its proximal end. The plunger also has a stepped-down section of reduced relative diameter located proximal to the distal tip of the plunger shaft.

The graft retention assembly comprises a collar and a set of tabs, which are disposed within the apertures of the tube. The tabs are biased towards each other but are capable of being displaced away from each other to receive or release the osteochondral graft. The graft retention assembly is attached to the tube at the annular recess by means of the collar. Movement of the shaft of the plunger distally within the tube causes the tabs of the graft retention assembly to be displaced away from each other.

The handle, positioned at the proximal end of the tube, comprises a bore extending from a proximal end to a distal end. The bore has an inside diameter at its distal end sufficient to accept an outside diameter of the proximal end of the tube. The handle also has an annular recess located at the proximal end of its bore that can accommodate a pliable material providing frictional engagement with the shaft of the plunger.

In accordance with another aspect of the present invention, there is provided a method of implanting an osteochondral graft to a recipient site using a delivery device of the present invention. The method comprises loading the osteochondral graft into the device by inserting the distal tip of the plunger into the proximal end of the tube, moving the plunger distally in the bore of the tube until the distal tip of the plunger engages the first protrusion causing the tabs of the graft retention assembly to be displaced away from each other, and inserting the osteochondral graft into the distal end of the tube. The plunger is then moved distally in the bore of the tube further until the first protrusion no longer engages the distal tip of the plunger and the first protrusion engages the stepped-down section of the plunger, causing the tabs of the graft retention assembly to move inwardly and come in contact with and secure the osteochondral graft. To implant the osteochondral graft, the delivery device with an adjacent osteochondral graft is positioned adjacent the recipient site. The osteochondral graft is delivered by moving the plunger distally in the bore of the tube further to extrude the osteochondral graft from the delivery device.

The features and advantages of the present invention will be readily apparent to those skilled in the art. While numerous changes may be made by those skilled in the art, such changes are within the spirit of the invention.

BRIEF DESCRIPTION OF THE DRAWINGS

These drawings illustrate certain aspects of some of the embodiments of the present invention, and should not be used to limit or define the invention.

FIG. 1 is an elevational view of a delivery device of the present invention with plunger inserted.

FIG. 2 is a cross-sectional view of the delivery device and plunger of FIG. 1.

DESCRIPTION OF PREFERRED EMBODIMENTS

Figure 3:
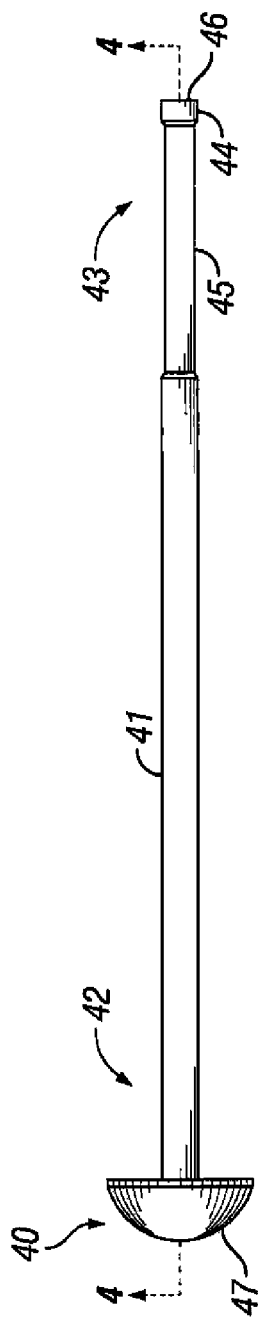
FIG. 3 is an elevational view of a plunger of the present invention.

The present invention relates to instrumentation used in implantation of an osteochondral graft, more particularly, to a delivery device used in inserting the osteochondral graft in a previously prepared hole. The invention also relates to the use of the delivery device to implant an osteochondral graft. The invention has particular utility in repairing localized damage to bone and cartilage, such as lesions and other defects in an articular surface of the knee or other weight-articulating joints.

The delivery device of the present invention can be used for the implantation of grafts from various locations and sources. The delivery device of the present invention can be used or adapted for use with osteochondral grafts, bone-only grafts, or cartilage-only grafts, as well as grafts of other construction, including artificial grafts, such as non-tissue grafts made from metals and synthetic materials. Similarly, the device of the present invention can be used or adapted for use with autografts, allografts, and xenografts. The preferred use of the delivery device is for the implantation of osteochondral allografts.

The delivery device of the present invention provides a means for securely holding onto the osteochondral graft so that it is not displaced from the delivery device prematurely while simultaneously avoiding damage to the osteochondral graft.

In accordance with various embodiments of the present invention, the delivery device generally includes the following components: a tube, a plunger, a handle, and a graft retention assembly.

In the descriptions of these components that follow, various preferences for materials of construction are generally expressed. Typically, polymeric materials or stainless steel are employed. The use of other materials of construction for the components, beyond any expressed preferences, is within the scope of the present invention. Generally, any materials of construction can be used for a component as long as the function of the component is not defeated and the material of construction is considered acceptable for a surgical environment.

Similarly, in the descriptions of the components that follow, various preferences regarding whether a component is transparent, translucent, or opaque may be expressed. Notwithstanding any such expressed preferences, the optical properties of a component may be varied as long as the function of the component is not defeated and the optical properties are considered acceptable for the intended surgical environment.

It is contemplated that the delivery device of the present invention may be fabricated in various sizes to accommodate osteochondral grafts of different diameters. In some embodiments, an indicator of the delivery device to be used with an osteochondral graft of a given diameter is provided. In particularly preferred embodiments, the indicator includes a marking in the form of color-coding associated with the delivery device corresponding to a particular osteochondral graft diameter. Preferably, any other instruments within a surgical set that are tailored for use with the same osteochondral graft diameter will have similar markings.

Referring generally to FIGS. 1, 2, 5 and 11, a delivery device 10 includes tube 30. Preferably, tube 30 is formed from a polymeric material. Preferably tube 30 is transparent or translucent. Tube 30 has a proximal end 31, a distal end 32, an outside diameter 23, and a bore 34 extending from proximal end 31 to distal end 32. Bore 34 has an inside diameter 25. The inside diameter 25 of bore 34, particularly at the distal 32 end of tube 30, is of sufficient size to accept insertion of the osteochondral graft intended for use in the surgery. Desirably, the inside diameter 25 of bore 34 at the distal 32 end of tube 30 is slightly larger, preferably around 0.5 mm larger, than the diameter of osteochondral graft.

The inside diameter 25 (corresponding to inside surface 35) of bore 34 is desirably constant from proximal end 31 to distal end 32. The outside diameter 23 (corresponding to outside surface 33) of tube 30 may also be substantially constant from proximal end 31 to distal end 32. However, in various embodiments, outside surface 33 of tube 30 may have an area of reduced diameter, such as in the form of an annular recess 37 or a step. Annular recess 37 is described further in the context of apertures 38 and graft retention assembly. In various embodiments, the outer surface 33 of tube 30 may taper down toward distal end 32, for example, to achieve an area of reduced wall thickness at the distal tip 36. In certain embodiments, a 1 mm wall thickness is preferred at distal tip 36.

Located on the distal end of tube 30, proximal to distal tip 36 (between distal tip 36 and annular recess 37, when present) are apertures 38 for accommodating descending tabs of the graft retention assembly. Preferably, a set of, preferably two, apertures 38 in the form of opposing cutout panes or windows are formed in the tube 30. In alternative embodiments, a single aperture may be employed. Preferably, apertures 38 terminate distally short of distal tip 36, such that distal tip 36 exists in the form of a continuous annular surface.

Figure 4:
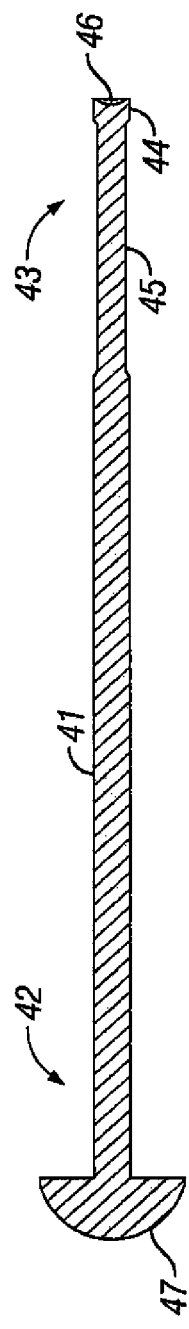
FIG. 4 is a cross-sectional view of the plunger of FIG. 3.
Figure 5:
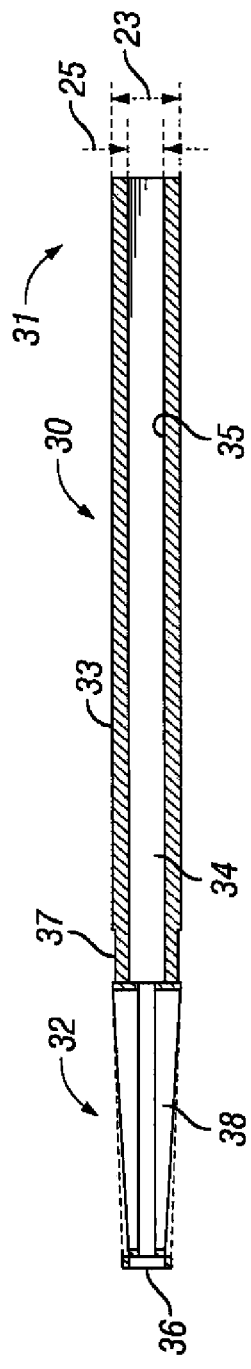
FIG. 5 is a cross-sectional view of the tube portion of a delivery device of the present invention.

Referring generally to FIGS. 2, 3 and 4, delivery device 10 has a plunger 40. Plunger 40, preferably formed from a polymeric material, is slidably disposed within bore 34 of tube 30. Plunger 40 has a shaft 41 with a proximal end 42 and distal end 43. During use of the delivery device 10, it is the distal movement of plunger 40 that causes an inserted osteochondral graft to be displaced from the delivery device 10 and implanted into the previously excised hole.

Desirably, the diameter of shaft 41 at distal tip 44 of distal end 43 substantially corresponds to the diameter of osteochondral graft. Among other benefits, this correspondence in diameter minimizes the likelihood of damage to osteochondral graft. Proximal to distal tip 44, shaft 41 has a stepped-down section 45 with a diameter smaller than that of the diameter of shaft 41 at distal tip 44. As will be described further in the context of graft retention assembly, stepped-down section 45 facilitates interaction between shaft 41 and graft retention assembly. Preferably, chamfers are provided where sections of shaft 41 having different diameters meet. In various embodiments, distal tip 44 desirably has a mating surface 46 adapted to engage osteochondral graft that is concave. In such embodiments, the concavity is preferably about 1 mm. In other embodiments, the mating surface 46 may have no curvature or may be convex.

Desirably, plunger 40 has a plunger handle 47 positioned at the proximal end 42 of shaft 41 to provide a means for gripping and depressing plunger 40. In preferred embodiments, plunger handle 47 is in the form of an enlarged button or other shape that serves as a stop against further distal movement of plunger 40. The plunger handle 47 may have an impacting surface adapted for manual depressing of the plunger 40 or for the use of a surgical hammer, mallet, or other instrument in mechanically depressing the plunger 40. The length of the plunger 40 can be tailored to achieve a desired osteochondral graft insertion depth. For example, plunger 40 can be tailored such that when it is fully depressed, the distal tip 44 may be retracted from, flush with, or extend past distal tip 36 of tube 30. For example, in certain embodiments, it may be desirable for plunger 40, when fully depressed, to remain from about 1 mm to about 2 mm retracted from distal tip 36 of tube 30. In use, this results in an implanted osteochondral graft that is about 1 mm to about 2 mm proud in the recipient hole.

Figure 9:
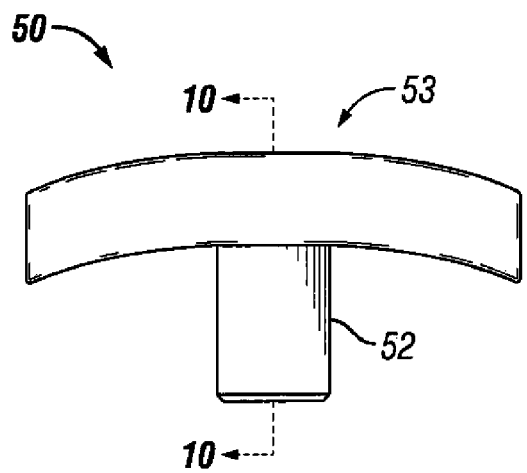
FIG. 9 is an elevational view of a handle of the present invention.
Figure 10:
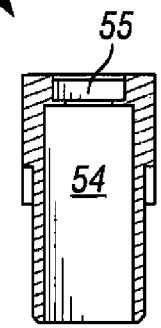
FIG. 10 is a cross-sectional view of the handle of FIG. 9.
Figure 11:
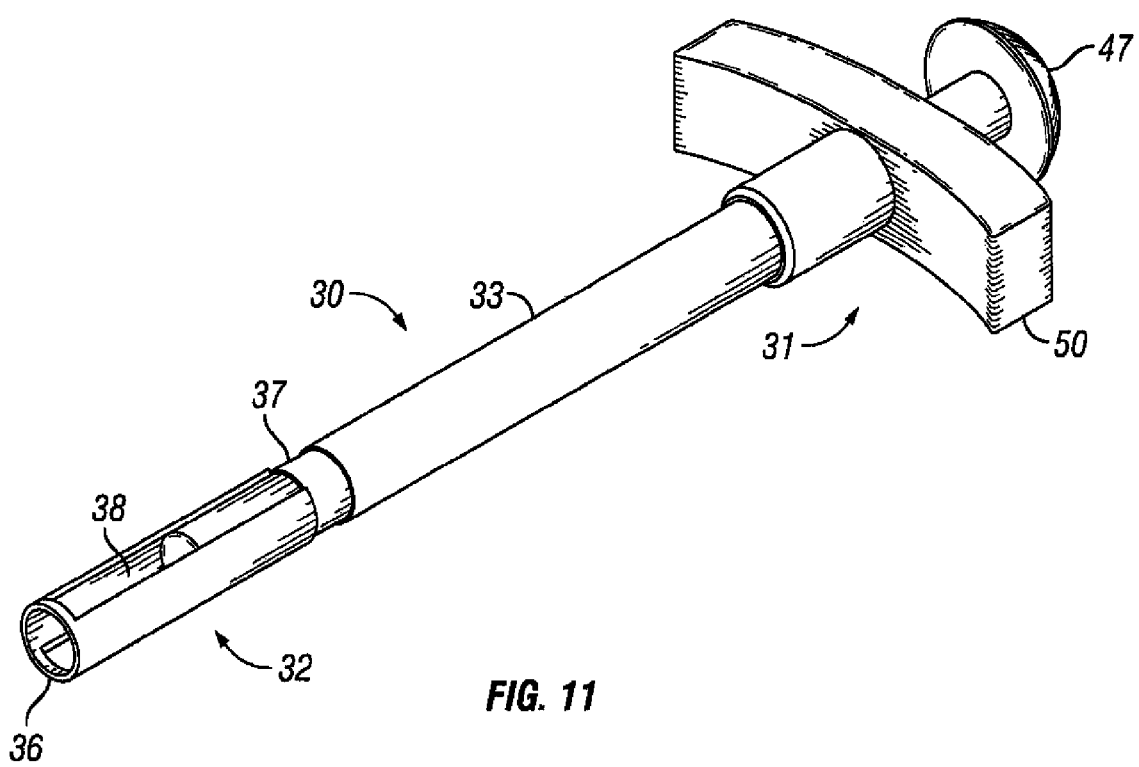
FIG. 11 is an elevational view of a delivery device of the present invention without a spring tab assembly.

Referring generally to FIGS. 1, 9 and 10, a handle 50, preferably formed from a polymeric material, is desirably positioned at the proximal end 31 of tube 30 to provide a means for gripping delivery device 10. In certain embodiments, handle 50 is integral to tube 30. Preferably, handle 50 is a separate component that is assembled onto the proximal end 31 of tube 30. In such embodiments, handle 50 can be viewed as having a distal end 52, a proximal end 53, and a bore 54 extending from the distal end 52 to the proximal end 53. In such embodiments, the distal end 52 of handle 50 is adapted for connection to the proximal end 31 of tube 30. Preferably, the proximal end 31 of tube 30 and the distal end 52 of handle 50 are sized such that the distal end 52 of handle 50 fits over the proximal end 31 of tube 30. The connection can be by friction fit, which is desirable, and/or secured by adhesive. The connection may also be by screw fit or other means. A desirable shape for handle 50 is a T-shaped contoured handle, such as depicted in FIG. 9.

Referring generally to FIG. 2, in embodiments where handle 50 is a separate component, the bore 54 at the proximal end 53 of handle 50 is of a diameter sufficient to allow slidable passage of plunger 40. Preferably, the inside diameter of bore 54 (corresponding to the inside surface of bore 54) at the proximal end 53 of handle 50 substantially corresponds to the inside diameter of tube 30. In preferred embodiments, an annular recess 55 (an area of increased inside diameter) is located within bore 54 at the proximal end 53 of handle 50. A pliable material, preferably a polymer o-ring, is disposed within the annular recess 55 that provides frictional engagement with shaft 41 of plunger 40. The o-ring acts as a seal that, during use of the delivery device 10, reduces, and preferably precludes, fluid within the joint cavity from flowing up through tube 30 and out of proximal end 31 of delivery device 10.

Figure 6:
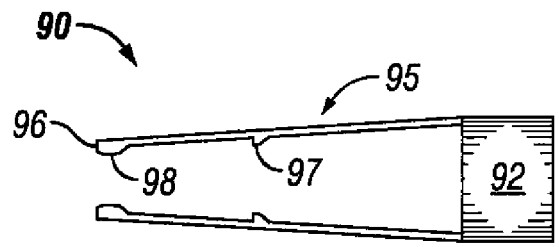
FIG. 6 is an elevational view of a spring tab assembly of the present invention.
Figure 7:
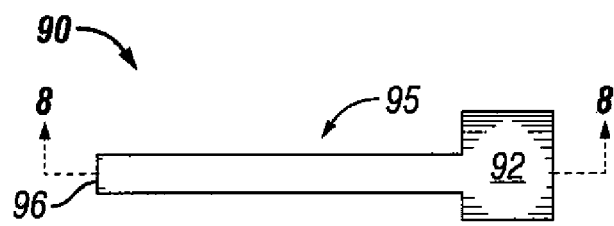
FIG. 7 is an elevational view of the spring tab assembly of FIG. 6 from a different angle.
Figure 8:
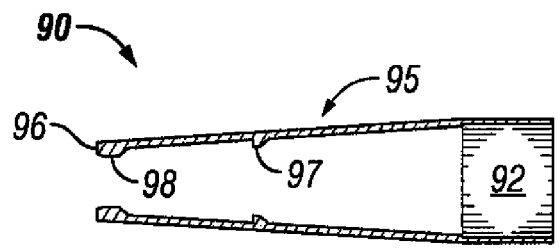
FIG. 8 is a cross-sectional view of the spring tab assembly of FIG. 7.

The delivery device 10 also has a graft retention assembly adapted for attachment to tube 30. In various embodiments, such as depicted in FIGS. 6, 7 and 8, the graft retention assembly is a spring tab assembly 90. Spring tab assembly 90 has a collar 92 that is adapted for attachment to tube 30. Spring tab assembly 90 also has a set of opposing tabs 95, corresponding preferably in number to the number of apertures 38, extending distally from collar 92, and terminating in distal tips 96. Spring tab assembly 90 is attached to tube 30 such that the tabs 95 reside within cutout panes 38. The method by which collar 92 is attached to tube 30 is not generally limited. In preferred embodiments, collar 92 is attached at and resides in annular recess 37 of tube 30. In preferred embodiments, collar 92 has a transverse slot that allows snap-fit attachment of collar 92 to tube 30.

Tabs 95 are biased, i.e., bent, towards each other when in a relaxed state but are capable of being expanded outwardly to receive and release the osteochondral graft. Desirably, the tabs 95 are bent equally from the points where they connect to the collar 92. In preferred embodiments, the extent of the bending is such that the protrusions 98 are a distance apart which is between 50-100% of the given graft diameter. Once osteochondral graft is positioned between tabs 95 and the force causing tabs 95 to expand is removed, the tabs 95 will move towards each other once again, coming in contact with and securing osteochondral graft. Preferably, the pressure exerted by the tabs 95 on the osteochondral graft is such that the tabs 95 provide enough static friction with the osteochondral graft so that it is not able to exit the delivery device 10 without the aid of the plunger 40 or other means. However, the force exerted by the tabs 95 should also not damage the osteochondral graft.

The expansion of tabs 95 to accept osteochondral graft and the subsequent inward movement of tabs 95 to secure osteochondral graft is the result of movement of shaft 41 of plunger 40 distally within tube 30. To facilitate the outward and inward movement of tabs 95, an inward facing first protrusion 97 is positioned on one or more of tabs 95. Preferably, an inward facing first protrusion 97 is positioned on each of tabs 95. First protrusion 97 is positioned proximal to distal tip 96. Preferably, first protrusion 97 is positioned half-way along the length of tabs 95.

As plunger 40 is depressed, distal tip 44 of shaft 41 first comes in contact with first protrusion 97, causing expansion of tabs 95 and facilitating insertion of osteochondral graft without risk of damage. Once the osteochondral graft has been inserted, plunger 40 is depressed further so that the first protrusion 97 engages the reduced diameter region of stepped-down section 45. First protrusion 97, depending upon the extent of the bending of tabs 95, may or may not actually come into physical contact with the shaft 41 of plunger 40 within the stepped-down section 45. At this point, tabs 95 will move towards each other once again, coming in contact with and securing osteochondral graft. In use, osteochondral graft is desirably secured within delivery device 10 with some portion of the graft extending beyond distal tip 36 of tube 30. This facilitates implantation of osteochondral graft in the previously prepared hole. For a desirable osteochondral graft having a length of about 10 mm, the graft, inserted and secured in the delivery device, extends desirably from about 0.5 mm to about 2 mm beyond distal tip 36 of tube 30, preferably about 2 mm beyond distal tip 36 of tube 30.

Due to the need for inward and outward movement of opposing fingers 95, spring tab assembly 90, and particularly opposing fingers 95, is preferably formed from stainless steel and is heat set in a bent state with opposing fingers 95 biased towards each other. In alternative embodiments, spring-biased polymeric materials or other biocompatible metals with appropriate flexibility may be employed. Other shape-memory materials may be employed.

In preferred embodiments of delivery device 10, an inward facing second protrusion 98 is positioned at or in proximity to distal tip 96 of one or more of tabs 95. Preferably, an inward facing second protrusion 98 is positioned on each of tabs 95. Second protrusion 98 facilitates gripping of osteochondral graft and reduces the likelihood of damaging osteochondral graft. A radius edge is desirably applied to the edges of the second protrusion 98 to further reduce the likelihood of damaging osteochondral graft. Desirably, a radius edge is applied to all the edges of the spring tab assembly 90. In various embodiments, a radius edge of about 1 mm is desirably employed on all edges of the spring tab assembly 90.

Having described the components of the delivery device 10, its use for implanting an osteochondral graft in a previously prepared hole is readily apparent but is described now in greater detail.

The distal tip 44 of plunger 40 is inserted into the proximal end 31 of tube 30 and moved distally within tube 30 until distal tip 44 engages first protrusion 97 of spring clip assembly 90. This causes the outward expansion of tabs 95. With tabs 95 now spread apart, a osteochondral graft is inserted, cartilage end first, into the distal end 32 of tube 30. Desirably, the osteochondral graft is left extending, preferably from about 1 mm to 2 mm, beyond distal tip 36 of tube 30.

The plunger 40 is now depressed further until first protrusion 97 is no longer in contact with the larger diameter of distal tip 44 of plunger 40. With first protrusion 97 now engaged with the reduced diameter region of stepped-down section 45, tabs 95 move towards each other, with distal tip 96, including second protrusion 98, if present, of tabs 95 coming in contact with and securing the osteochondral graft.

The delivery device 10 and the osteochondral graft are now ready to be used to implant the osteochondral graft into the recipient site, i.e., previously-prepared hole. In various embodiments of the present invention, the delivery device 10 may be used with a cannulated delivery guide that has a bore with an inside diameter sized to accommodate slidable passage of the delivery device 10. The delivery guide will preferably be made of a polymeric material but other materials of construction are contemplated. Similarly, the delivery guide may be transparent, translucent, or opaque. The delivery guide may be used to retract soft tissues (e.g., the naturally occurring fat pad) between the surgical incision or arthroscopic portal and the recipient site. In some embodiments, the delivery guide will generally be prepositioned over the prepared recipient site.

With or without the delivery guide, the delivery device 10 is positioned directly above, and preferably in contact with, the recipient site. The osteochondral graft is extruded from the delivery device 10 by depressing the plunger 40 until further distal movement of the plunger 40 is limited by the plunger handle 47, other stop, or complete insertion of the osteochondral graft in the recipient site. The delivery device 10 can then be removed from the surgical site. If the osteochondral graft remains proud, a tamp or other instrument can be used to further insert the osteochondral graft such that it is flush with the surrounding articular cartilage.

The delivery device 10 may be provided to a surgeon preassembled in its entirety. Alternatively, the component parts or some less-than-complete assemblage of the components parts may be provided for final assembly at some point prior to its use in implanting the osteochondral graft. For example, as provided to the surgeon, the plunger 40 may not already be inserted into tube 30.

Assembly of the delivery device 10 is readily straightforward and apparent to one of ordinary skill in the art having the benefit of this disclosure. In accordance with various embodiments described herein, handle 50, if not integral with tube 30, is attached to the proximal end 31 of tube 30. O-ring is placed within the annular recess 55 disposed in the inner surface of the proximal end 53 of the bore 54 of the handle 50. Spring tab assembly 90 is attached to the tube 30 such that tabs 95 reside in apertures 38. The distal tip 44 of plunger 40 is inserted into the proximal end 31 of tube 30 (initially through the proximal end of handle 50 if the handle 50 is not integral with tube 30).

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. For example, while the primary intended use of the delivery device of the present invention is for use in implanting osteochondral grafts, it is envisioned that the delivery device could be used for implanting other tissue implants. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. The indefinite articles "a" or "an", as used in the claims, are defined herein to mean one or more than one of the element that it introduces.

What is claimed is:

1. A delivery device for an osteochondral graft comprising:
   a) a tube comprising: a bore having an inside diameter and extending from a proximal end to a distal end, wherein the inside diameter of the bore is sufficient to accept an osteochondral graft of a desired diameter; and a set of apertures located adjacent the distal end of the tube;
   b) a plunger slidably disposed within the bore of the tube comprising a shaft having a proximal end, distal end, and distal tip;
   c) a graft retention assembly comprising a collar coupled to the tube and a set of tabs, said tabs disposed within the apertures of the tube, wherein the tabs are biased towards each other but are capable of being displaced away from each other to receive or release the osteochondral graft.

2. A delivery device in accordance with claim 1, wherein the retention assembly is a spring tab assembly.

3. A delivery device in accordance with claim 1, wherein the set of apertures is a set of opposing cutout panes.

4. A delivery device in accordance with claim 1, further comprising: a handle positioned at the proximal end of the tube, the handle comprising a bore extending from a proximal end to a distal end, the bore having an inside diameter at its distal end sufficient to accept an outside diameter of the proximal end of the tube.

5. A delivery device in accordance with claim 4, the handle further comprising an annular recess located at the proximal end of its bore and pliable material disposed within the annular recess that provides frictional engagement with the shaft of the plunger.

6. A delivery device in accordance with claim 1, further comprising an annular recess along an outside diameter of the tube proximal to the apertures, wherein the graft retention assembly is attached to the tube at the annular recess by means of the collar.

7. A delivery device in accordance with claim 6, wherein the collar is attached to the annular recess along the outside diameter of the tube by snap-fit connection.

8. A delivery device in accordance with claim 1, wherein movement of the shaft of the plunger distally within the tube causes the tabs of the graft retention assembly to be displaced away from each other.

9. A delivery device in accordance with claim 1, further comprising an inward facing first protrusion on one or more of the tabs of the graft retention assembly engageable with the distal tip of the shaft of the plunger to cause the tabs of the graft retention assembly to be displaced away from each other.

10. A delivery device in accordance with claim 1, further comprising an inward facing second protrusion on one or more of the tabs of the graft retention assembly engageable with the osteochondral graft.

11. A delivery device in accordance with claim 1, the plunger further comprising a plunger handle positioned at its proximal end.

12. A delivery device in accordance with claim 1, the plunger handle comprising an enlarged impact surface.

13. A delivery device in accordance with claim 1, the shaft of the plunger having a stepped-down section of reduced diameter relative to the diameter of the distal tip of the plunger shaft, the stepped-down section positioned proximal to the distal tip of the plunger shaft.

14. A delivery device for an osteochondral graft comprising:
   a) a tube comprising: a bore having an inside diameter and extending from a proximal end to a distal end, wherein the inside diameter of bore is sufficient to accept an osteochondral graft of a desired diameter; a set of apertures located adjacent the distal end of the tube; and an annular recess along an outside diameter of tube proximal to the apertures;
   b) a plunger slidably disposed within the bore of the tube comprising a shaft having a proximal end, distal end and distal tip, having a plunger handle positioned at its proximal end, and having a stepped-down section of reduced diameter relative to the diameter of the distal tip of the plunger shaft, the stepped-down section located proximal to the distal tip of the plunger shaft;
   c) a graft retention assembly comprising a collar coupled to the tube and a set of tabs, said tabs disposed within the apertures of the tube, wherein the tabs are biased towards each other but are capable of being displaced away from each other to receive or release the osteochondral graft, wherein the graft retention assembly is attached to the tube at the annular recess by means of the collar, wherein movement of the shaft of the plunger distally within the tube causes the tabs of the graft retention assembly to be displaced away from each other; and
   d) a handle positioned at the proximal end of the tube comprising a bore extending from a proximal end to a distal end, the bore having an inside diameter at its distal end sufficient to accept an outside diameter of the proximal end of the tube, the handle further comprising an annular recess located at the proximal end of its bore and pliable material disposed within the annular recess that provides frictional engagement with the shaft of the plunger.

15. A delivery device in accordance with claim 14, wherein the pliable material comprises an o-ring.

16. A delivery device in accordance with claim 14, wherein the collar is attached to the annular recess along the outside diameter of the tube by snap-fit connection.

17. A delivery device in accordance with claim 14, further comprising an inward facing first protrusion on one or more of the tabs of the graft retention assembly engageable with the distal tip of the shaft of the plunger to cause the tabs of the graft retention assembly to be displaced away from each other.

18. A delivery device in accordance with claim 14, further comprising an inward facing second protrusion on one or more of the tabs of the graft retention assembly engageable with the osteochondral graft.

19. A delivery device in accordance with claim 14, the plunger handle comprising an impact surface.

20. A method of implanting an osteochondral graft to a recipient site using a delivery device comprising:
   a) a tube comprising: a bore having an inside diameter and extending from a proximal end to a distal end, wherein the inside diameter of the bore is sufficient to accept an osteochondral graft of a desired diameter; and a set of apertures located adjacent the distal end of the tube;
   b) a plunger slidably disposed within the bore of the tube comprising a shaft having a proximal end, distal end, and distal tip, and having a stepped-down section of reduced diameter relative to the diameter of the distal tip, the stepped-down section positioned proximal to the distal tip of the plunger shaft; and
   c) a graft retention assembly comprising a collar coupled to the tube and a set of tabs, said tabs disposed within the apertures, wherein the tabs are biased towards each other but are capable of being displaced away from each other to receive or release the osteochondral graft, and further comprising an inward facing first protrusion on one or more of the tabs of the graft retention assembly engageable with the distal tip of the shaft of the plunger to cause the tabs of the graft retention assembly to be displaced away from each other;
   the method comprising:
   loading the osteochondral graft into the device by inserting the distal tip of the plunger into the proximal end of the tube, moving the plunger distally in the bore of the tube until the distal tip of the plunger engages the first protrusion causing the tabs of the graft retention assembly to be displaced away from each other, inserting the osteochondral graft into the distal end of the tube, and moving the plunger distally in the bore of the tube further until the first protrusion no longer engages the distal tip of the plunger and the first protrusion engages the stepped-down section of the plunger, causing the tabs of the graft retention assembly to move inwardly and come in contact with and secure the osteochondral graft;

positioning the delivery device with osteochondral graft adjacent the recipient site; and delivering the osteochondral graft by moving the plunger distally in the bore of the tube further to extrude the osteochondral graft from the delivery device.

\* \* \* \* \*

UNITED STATES PATENT AND TRADEMARK OFFICE
CERTIFICATE OF CORRECTION

PATENT NO. : 8,435,305 B2
APPLICATION NO. : 12/873049
DATED : May 7, 2013
INVENTOR(S) : Lozier et al.

Page 1 of 3

It is certified that error appears in the above-identified patent and that said Letters Patent is hereby corrected as shown below:

Title Page

On page 3, in column 1, under Item (56) "Other Publications", line 21, delete "V," and insert --V.,--, therefor On page 3, in column 1, under Item (56) "Other Publications", line 25, delete "F.R.," and insert --F. R.,--, therefor On page 3, in column 1, under Item (56) "Other Publications", line 28, delete "W," and insert --W.,--, therefor On page 3, in column 1, under Item (56) "Other Publications", line 33, delete "M," and insert --M.,--, therefor On page 3, in column 1, under Item (56) "Other Publications", line 36, delete "C," and insert --C.,--, therefor On page 3, in column 1, under Item (56) "Other Publications", line 40, delete "F," and insert --F.,--, therefor On page 3, in column 1, under Item (56) "Other Publications", line 43, delete "L," and insert --L.,--, therefor On page 3, in column 1, under Item (56) "Other Publications", line 46, delete "L," and insert --L.,--, therefor On page 3, in column 1, under Item (56) "Other Publications", line 48, delete "tenique" and insert --technique--, therefor Signed and Sealed this
First Day of October, 2013

Teresa Stanek Rea
*Deputy Director of the United States Patent and Trademark Office*

On page 3, in column 1, under Item (56) "Other Publications", line 65, delete "Knieinstabi1itat" and insert --Knieinstabilitat--, therefor On page 3, in column 2, under Item (56) "Other Publications", line 3, delete "Sever" and insert --Severe--, therefor On page 3, in column 2, under Item (56) "Other Publications", line 6, after "Kniegelenk", insert --)--, therefor On page 3, in column 2, under Item (56) "Other Publications", line 13, delete "sever" and insert --severe--, therefor On page 3, in column 2, under Item (56) "Other Publications", line 22, delete "W," and insert --W.,--, therefor On page 3, in column 2, under Item (56) "Other Publications", line 24, delete "T," and insert --T.,--, therefor On page 3, in column 2, under Item (56) "Other Publications", line 36, delete "mailed" and insert --filed--, therefor On page 3, in column 2, under Item (56) "Other Publications", line 50, delete "flied" and insert --filed--, therefor On page 3, in column 2, under Item (56) "Other Publications", line 59, delete "filed" and insert --mailed--, therefor On page 4, in column 1, under Item (56) "Other Publications", line 37, before "International", insert --"--, therefor On page 4, in column 1, under Item (56) "Other Publications", line 38, delete "2009" and insert --2009",--, therefor On page 4, in column 2, under Item (56) "Other Publications", line 42, delete "H," and insert --H.,--, therefor In the Specification In column 4, line 51, delete "distal 32 end" and insert --distal end 32--, therefor In column 4, line 54, delete "distal 32 end" and insert --distal end 32--, therefor In column 5, line 8, before "in", insert --is--, therefor

CERTIFICATE OF CORRECTION (continued)
U.S. Pat. No. 8,435,305 B2

In the Claims

In column 8, line 59, in Claim 1, before "the", insert --to--, therefor

In column 9, line 54, in Claim 14, before "the", insert --to--, therefor

In column 10, line 39, in Claim 20, before "the", insert --to--, therefor

In column 11, line 4, in Claim 20, before "the", insert --to--, therefor